United States Patent
Monteleone et al.

(10) Patent No.: US 8,709,993 B2
(45) Date of Patent: *Apr. 29, 2014

(54) QUINAZOLINE COMPOUNDS AND THEIR USE IN PERFUME COMPOSITIONS

(75) Inventors: Michael G. Monteleone, Hazlet, NJ (US); Robert P. Belko, Monroe Township, NJ (US); Franc T. Schiet, Naarden (NL); Paul D. Jones, Aberdeen, NJ (US); Anthony T. Levorse, Jr., Westfield, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 624 days.

This patent is subject to a terminal disclaimer.

(21) Appl. No.: 13/027,314

(22) Filed: Feb. 15, 2011

(65) Prior Publication Data

US 2012/0207697 A1    Aug. 16, 2012

(51) Int. Cl.
   *C11B 9/00*     (2006.01)
   *C07D 239/26*   (2006.01)

(52) U.S. Cl.
   CPC ............. *C07D 239/26* (2013.01); *C11B 9/0092* (2013.01)
   USPC .............................. 512/10; 514/267; 544/249

(58) Field of Classification Search
   CPC ............................ C07D 239/26; C11B 9/0092
   USPC .................. 514/267, 772; 544/249; 510/103; 424/762; 512/10
   See application file for complete search history.

(56) References Cited

U.S. PATENT DOCUMENTS 8,557,876 B2 *  10/2013  Belko et al. .................. 514/788

* cited by examiner

*Primary Examiner* — Erich A Leeser
(74) *Attorney, Agent, or Firm* — Elizabeth M. Quirk; XuFan Tseng; Joseph F. Leightner

(57) ABSTRACT

The present invention relates to novel quinazoline compounds and their use in perfume compositions. The novel quinazoline compounds of the present invention are represented by the following formula:

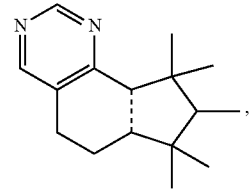

an isomer or a mixture of isomers thereof,
wherein the broken line represents a single or double bond.

7 Claims, No Drawings

QUINAZOLINE COMPOUNDS AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel compounds and their unexpected advantageous use in enhancing, improving or modifying the fragrance of perfumes, colognes, toilet water, fabric care products, personal products and the like.

More specifically, the present invention relates to novel quinazoline compounds represented by Formula I set forth below:

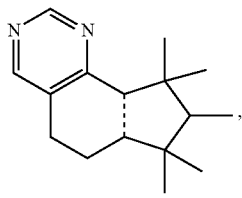

Formula I isomers or mixtures of isomers thereof, wherein the broken line represents a single or double bond.

Another embodiment of the present invention relates to a fragrance composition comprising the novel compounds provided above.

Another embodiment of the present invention relates to a fragrance product comprising the compounds provided above.

Another embodiment of the present invention relates to a method of improving, enhancing or modifying a fragrance formulation through the addition of an olfactory acceptable amount of the novel compounds provided above.

These and other embodiments of the present invention will be apparent by reading the following specification.

DETAILED DESCRIPTION OF THE INVENTION

The compounds of the present invention may be represented by the following structures:

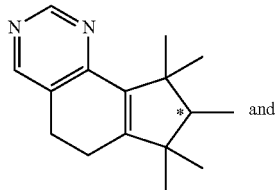

Formula II and

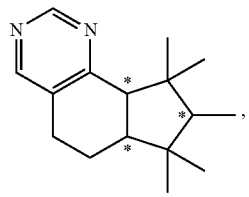

Formula III wherein * indicates a chiral center.

The isomeric forms of Formula II and Formula III may be further represented, respectively, by the following structures:

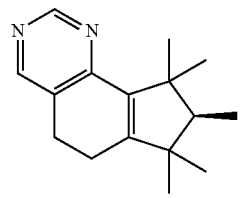

Formula IV

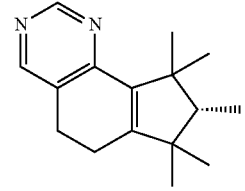

Formula V

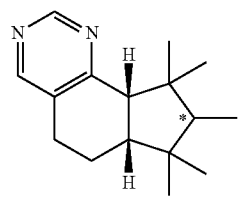

Formula VI

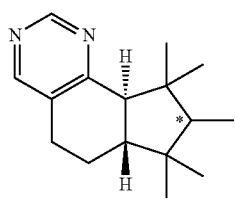

Formula VII

Those with the skill in the art will appreciate that

Formula II is 6,7,8,9-tetrahydro-7,7,8,9,9-pentamethyl-5H-cyclopenta[H]quinazoline;

Formula III is 6,6a,7,8,9,9a-hexahydro-7,7,8,9,9-pentamethyl-5H-cyclopenta[H]quinazoline;

Formula IV is 8S-6,7,8,9-tetrahydro-7,7,8,9,9-pentamethyl-5H-cyclopenta[H]quinazoline;

Formula V is 8R-6,7,8,9-tetrahydro-7,7,8,9,9-pentamethyl-5H-cyclopenta[H]quinazoline;

Formula VI is cis-6,6a,7,8,9,9a-hexahydro-7,7,8,9,9-pentamethyl-5H-cyclopenta[H]quinazoline; and Formula VII is trans-6,6a,7,8,9,9a-hexahydro-7,7,8,9,9-pentamethyl-5H-cyclopenta[H]quinazoline.

The compounds of the present invention can be prepared from Cashmeran™ (commercially available at International Flavors & Fragrances Inc.) or its hydrogenated form according to the reaction scheme below, the details of which are specified in the Examples. Materials were purchased from Aldrich Chemical Company unless noted otherwise.

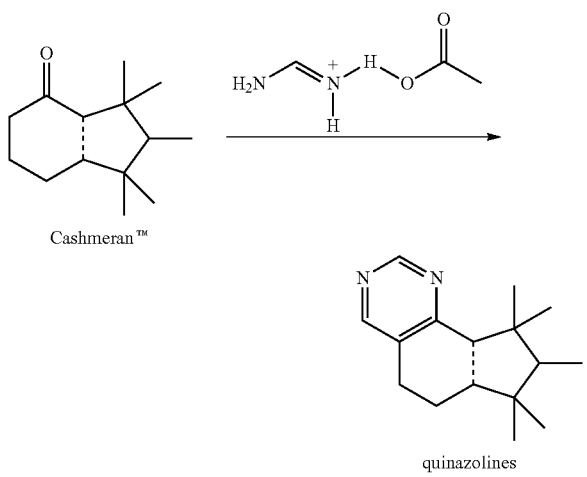

Additionally, a cis-hexahydro-quinazoline is obtained. A tetrahydro-quinazoline from the above scheme is further treated with isopropanol (referred to as "IPA" hereinafter) and palladium on carbon (referred to as "Pd/C" hereinafter) in the presence of hydrogen to provide 90% cis- and 10% trans-hexahydro-quinazolines.

Those with skill in the art will recognize that the isomeric products obtained as described above can be further separated using techniques known to those with skill in the art. Suitable techniques include, for example, distillation and chromatography such as high performance liquid chromatography, referred to as HPLC, particularly silica gel chromatograph, and gas chromatography trapping known as GC trapping. Yet, commercial products are mostly offered as isomeric mixtures.

The use of the compounds of the present invention is widely applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

The terms "fragrance formulation", "fragrance composition", and "perfume composition" are understood to mean the same and refer to a formulation that is intended for providing a fragrance character to a perfume, a cologne, toilet water, a personal product, a fabric care product, and the like. The fragrance formulation of the present invention is a composition comprising a compound of the present invention.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation this ingredient provides sweet, floral, ambery, musky, woody, and powdery notes to make the fragrance formulation more desirable and noticeable, and add the perception of value. The odor qualities found in this material assist in beautifying and enhancing the finished accord as well as improving the performance of the other materials in the fragrance.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, mol is understood to be mole, and mmHg be millimeters (mm) of mercury (Hg). IFF as used in the examples is understood to mean International Flavors & Fragrances Inc., New York, N.Y., USA.

Example I

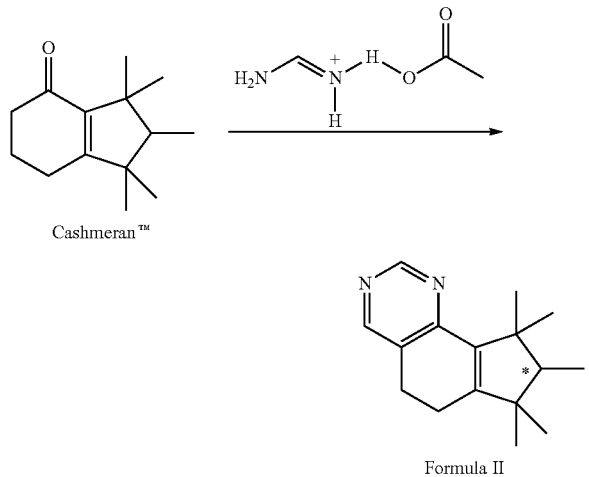

Cashmeran™

Formula II

Preparation of 6,7,8,9-tetrahydro-7,7,8,9,9-pentamethyl-5H-cyclopenta[H]quinazoline (Formula II)

A 5 L reaction vessel was charged with Cashmeran™ (412 g, 2.0 mol, commercially available at IFF), formamidine acetate (1030 g, 10.0 mol), and butanol (1.2 L). The reaction mixture was heated to 118° C. for 4 hours and then cooled to 25° C. The reaction mixture was washed twice with brine (1 L) and purified by vacuum distillation to afford 6,7,8,9-tetrahydro-7,7,8,9,9-pentamethyl-5H-cyclopenta[H]quinazoline (260 g) having a boiling point of 140° C. at a pressure of 1.6 mmHg Further recrystallization from ethanol afforded a solid with a melting point of 80.0° C.

$^1$H NMR (CDCl$_3$, 500 MHz): 8.90 ppm (s, 1H), 8.31 ppm (s, 1H), 2.77-2.82 ppm (m, 2H), 2.35-2.41 ppm (m, 1H), 2.25-2.32 ppm (m, 1H), 1.74 ppm (q, 1H, J=7.37 Hz), 1.38 ppm (s, 3H), 1.23 ppm (s, 3H), 1.11 ppm (s, 3H), 0.95 ppm (d, 3H, J=7.40 Hz), 0.93 ppm (s, 3H).

The compound was described as having musky, ambery, and powdery notes.

Example II

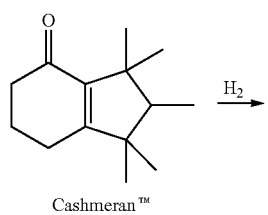

Cashmeran™

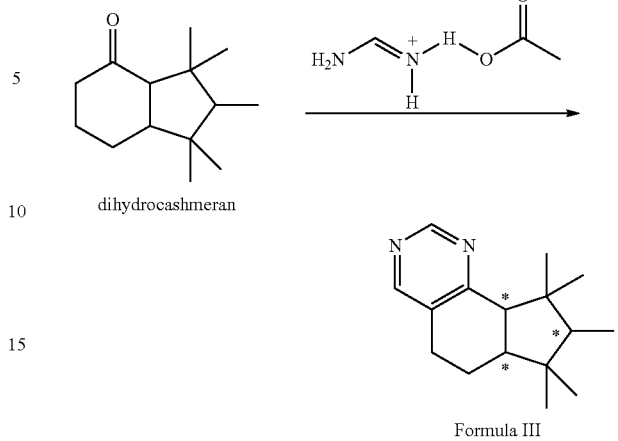

dihydrocashmeran

Formula III

Preparation of 6,6a,7,8,9,9a-hexahydro-7,7,8,9,9-pentamethyl-5H-cyclopenta[H]quinazoline (Formula III)

Dihydrocashmeran was obtained via the hydrogenation of Cashmeran™. A 3 L reaction vessel was charged with dihydrocashmeran (255 g, 1.2 mol), formamidine acetate (642 g, 6.2 mol), and butanol (1.2 L). The reaction mixture was heated to 118° C. for 4 hours and then cooled to 25° C. The reaction mixture was washed twice with brine (1 L) and purified by vacuum distillation to afford a 40:60 cis/trans mixture of 6,6a,7,8,9,9a-hexahydro-7,7,8,9,9-pentamethyl-5H-cyclopenta[H]quinazoline (200 g) having a boiling point of 153° C. at a pressure of 2.0 mmHg The cis/trans structures were confirmed by NMR analysis by GC trapping.

Trans-6,6a,7,8,9,9a-hexahydro-7,7,8,9,9-pentamethyl-5H-cyclopenta[H]quinazoline $^1$H NMR (CDCl$_3$, 500 MHz): 8.92 ppm (s, 1H), 8.37 ppm (s, 1H), 2.75-2.93 ppm (m, 2H), 2.65 ppm (d, J=12.6 Hz, 1H), 1.20-2.10 ppm (m, 4H), 1.32 ppm (s, 3H), 0.99 ppm (s, 3H), 0.95 ppm (s, 3H), 0.84 ppm (d, J=7.5 Hz, 3H), 0.71 ppm (s, 3H).

Cis-6,6a,7,8,9,9a-hexahydro-7,7,8,9,9-pentamethyl-5H-cyclopenta[H]quinazoline $^1$H NMR (CDCl$_3$, 500 MHz): 8.96 ppm (s, 1H), 8.39 ppm (s, 1H), 3.00 ppm (d, J=9.7 Hz, 1H), 2.52-2.79 ppm (m, 2H), 1.25-2.15 ppm (m, 4H), 1.42 ppm (s, 3H), 1.10 ppm (s, 3H), 0.92 ppm (s, 3H), 0.84 ppm (d, J=7.3 Hz, 3H), 0.54 ppm (s, 3H).

The compounds were described as having ambery, musky, and woody notes.

Example III

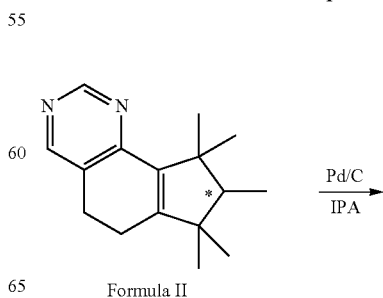

Formula II

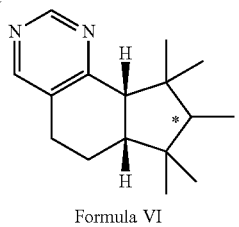

Formula VI

Preparation of cis-6,6a,7,8,9,9a-hexahydro-7,7,8,9,9-pentamethyl-5H-cyclopenta[H]quinazoline (Formula VI)

A 500 mL zipper autoclave was charged with 6,7,8,9-tetrahydro-7,7,8,9,9-pentamethyl-5H-cyclopenta[H]quinazoline (100 g, synthesized as above in EXAMPLE I), IPA (100 mL), and Pd/C (1 g). The autoclave was sealed, purged with nitrogen, and then pressurized with hydrogen. The reaction mixture was heated to 180° C. for 4 hours and subsequently cooled to 25° C. The autoclave was vented and purged with nitrogen. The catalyst was removed by filtration through celite. A crude mass containing the major product cis-6,6a,7,8,9,9a-hexahydro-7,7,8,9,9-pentamethyl-5H-cyclopenta[H]quinazoline (90%) was obtained. The crude mass was evaluated by gas chromatography olfactometry. Cis-6,6a,7,8,9,9a-hexahydro-7,7,8,9,9-pentamethyl-5H-cyclopenta[H]quinazoline was described as having a musky character. In addition, the minor product in the crude mass, trans-6,6a,7,8,9,9a-hexahydro-7,7,8,9,9-pentamethyl-5H-cyclopenta[H]quinazoline (Formula VII) (10%), was also evaluated and described as having an ambery character.

Example IV

The fragrance formulas exemplified as follows demonstrated that the addition of 6,6a,7,8,9,9a-hexahydro-7,7,8,9,9-pentamethyl-5H-cyclopenta[H]quinazoline (Formula III) containing a 40:60 cis/trans isomeric mixture provided a musky character to the fragrance formula.

| Ingredient | Parts (g) | Parts (g) |
|---|---|---|
| Kharismal ™ | 175 | 175 |
| Ethylene Brassylate | 50 | 50 |
| Dipropylene Glycol | 34 | 34 |
| Iso Gamma Super ™ | 30 | 30 |
| Hydroxy Citronellal Pure | 15 | 15 |
| Indasan | 10 | 10 |
| Amberiff 20% IPM | 10 | 10 |
| L-Citronellol | 8 | 8 |
| Beta Ionone Extra | 5 | 5 |
| Linalyl Acetate | 5 | 5 |
| Ambrettolide | 3 | 3 |
| Geraniol 980 | 3 | 3 |
| Healingwood ™ | 1 | 1 |
| Amber Xtreme ™ 1% DPG | 1 | 1 |
| Formula III | 10 | — |
| DPG | — | 10 |
| Total | 360 | 360 |

The above fragrance formulas had floral and woody characters. The addition of 6,6a,7,8,9,9a-hexahydro-7,7,8,9,9-pentamethyl-5H-cyclopenta[H]quinazoline (Formula III) intensified the floral and woody notes and provided a musky undertone.

Example V

Fragrance formulation containing 6,7,8,9-tetrahydro-7,7,8,9,9-pentamethyl-5H-cyclopenta[H]quinazoline (Formula II)

| Ingredient | Parts (g) |
|---|---|
| Santaliff ™ | 24 |
| Phenoxanol ™ | 32 |
| Coumarin | 28 |
| Cyclamal Extra | 1 |
| Eth Vanillin | 7 |
| Geraniol 980 Pure | 1 |
| Hedione ™ | 60 |
| Amy Cinnamic Aldehyde | 60 |
| Heliotropine | 17 |
| Hexyl Cinnamic Ald | 16 |
| Beta Ionone Extra | 6 |
| Iso E Super ™ | 70 |
| Lyral ™ | 16 |
| lillial ™ | 160 |
| Lilianth | 20 |
| Methyl Ionone Gamma A | 73 |
| Veramoss | 2 |
| Peru Balsam Oil India | 3 |
| Prenyl Acetate | 1 |
| Methyl Cedryl Ketone | 40 |
| Methyl Phenyl Acetate | 1 |
| Aubepine | 4 |
| Benzoin | 10 |
| Cedrol Tex | 3 |

Example V

Continued

| Ingredient | Parts (g) |
|---|---|
| Citronellol Extra | 3 |
| Geraniol Coeur | 4 |
| Methyl Cinnamate | 3 |
| Styrax Alva Ess | 2 |
| Vanillin ex Lignin | 12 |
| Cananga Java Native | 5 |
| Formula II | 20 |
| Total | 704 |

6,7,8,9-Tetrahydro-7,7,8,9,9-pentamethyl-5H-cyclopenta[H]quinazoline (Formula II) imparted diffusive floral and soft powdery characters to a fragrance formula.

What is claimed is:

1. A compound 6,7,8,9-tetrahydro-7,7,8,9,9-pentamethyl-5H-cyclopenta[H]quinazoline.

2. A fragrance formulation containing an olfactory acceptable amount of 6,7,8,9-tetrahydro-7,7,8,9,9-pentamethyl-5H-cyclopenta[H]quinazoline.

3. The fragrance formulation of claim 2 further comprising a product selected from the group consisting of a perfume, a cologne, toilet water, a cosmetic product, a personal care product, a fabric care product, a cleaning product, and an air freshener.

4. The fragrance formulation of claim 3, wherein the cleaning product is selected from the group consisting of a detergent, a dishwashing composition, a scrubbing compound, and a window cleaner.

5. The fragrance formulation of claim 2, wherein the olfactory acceptable amount is from about 0.005 to about 50 weight percent of the fragrance formulation.

6. The fragrance formulation of claim 2, wherein the olfactory acceptable amount is from about 0.5 to about 25 weight percent of the fragrance formulation.

7. The fragrance formulation of claim 2, wherein the olfactory acceptable amount is from about 1 to about 10 weight percent of the fragrance formulation.

\* \* \* \* \*